US012734255B2

(12) United States Patent
Goodrich et al.

(10) Patent No.: US 12,734,255 B2
(45) Date of Patent: Sep. 15, 2026

(54) RADIOPAQUE POLYMERS WITH ENHANCED RADIOPACITY

(71) Applicant: ENDOSHAPE, INC., Boulder, CO (US)

(72) Inventors: Stephen D. Goodrich, Boulder, CO (US); Jeffrey P. Castleberry, Boulder, CO (US)

(73) Assignee: Embolization, Inc., Boulder, CO (US)

( * ) Notice: Subject to any disclaimer, the term of this patent is extended or adjusted under 35 U.S.C. 154(b) by 996 days.

(21) Appl. No.: 16/346,920

(22) PCT Filed: Dec. 1, 2017

(86) PCT No.: PCT/US2017/064262
§ 371 (c)(1),
(2) Date: May 2, 2019

(87) PCT Pub. No.: WO2018/102714
PCT Pub. Date: Jun. 7, 2018

(65) Prior Publication Data
US 2020/0054770 A1 Feb. 20, 2020

Related U.S. Application Data

(60) Provisional application No. 62/429,433, filed on Dec. 2, 2016.

(51) Int. Cl.
*A61K 9/00* (2006.01)
*A61K 49/04* (2006.01)
(Continued)

(52) U.S. Cl.
CPC ...... *A61K 49/0442* (2013.01); *A61K 49/0447* (2013.01); *A61L 27/16* (2013.01);
(Continued)

(58) Field of Classification Search
CPC .................................................. A61K 49/0042
See application file for complete search history.

(56) References Cited

U.S. PATENT DOCUMENTS 5,162,396 A 11/1992 Hilty et al.
5,780,668 A * 7/1998 Rheinberger ........... C07C 69/76 564/163

(Continued)

FOREIGN PATENT DOCUMENTS

WO WO-2012019145 A1 * 2/2012 ......... A61K 49/0442

OTHER PUBLICATIONS

European Extended Search Report (EP 17876495.7) issued on Jun. 26, 2020.

(Continued)

*Primary Examiner* — Paul W Dickinson
(74) *Attorney, Agent, or Firm* — Bochner PLLC; Andrew D. Bochner; Caitlin A. Hyland

(57) ABSTRACT

Radiopaque polymer compositions and methods for making the compositions are provided. These radiopaque polymer compositions include polymer compositions comprising a crosslinked polymer network, the network comprising a first repeating unit derived from a monofunctional monomer, a second repeating unit derived from a crosslinker monomer having more than two polymerizable groups and a third repeating unit a derived from a crosslinker monomer having two or more polymerizable groups. Devices formed from radiopaque polymer compositions and methods for synthesizing radiopaque polymer compositions are also provided.

15 Claims, 5 Drawing Sheets

(51) Int. Cl.

| | |
|---|---|
| ***A61L 27/16*** | (2006.01) |
| ***A61L 27/50*** | (2006.01) |
| ***A61L 29/04*** | (2006.01) |
| ***A61L 29/18*** | (2006.01) |
| ***A61L 31/04*** | (2006.01) |
| ***A61L 31/18*** | (2006.01) |
| ***A61P 41/00*** | (2006.01) |

(52) U.S. Cl.

CPC ............ *A61L 27/50* (2013.01); *A61L 29/041* (2013.01); *A61L 29/18* (2013.01); *A61L 31/048* (2013.01); *A61L 31/18* (2013.01); *A61P 41/00* (2018.01); *A61L 2430/06* (2013.01)

(56) References Cited

U.S. PATENT DOCUMENTS

| | | | | |
|---|---|---|---|---|
| 6,040,408 | A | 3/2000 | Koole | |
| 6,160,148 | A | 12/2000 | Dauth et al. | |
| 6,387,981 | B1 | 5/2002 | Zhang et al. | |
| 9,062,141 | B2 | 6/2015 | Goodrich et al. | |
| 9,789,231 | B2 | 10/2017 | Goodrich et al. | |
| 2006/0024266 | A1 | 2/2006 | Brandom et al. | |
| 2006/0058451 | A1* | 3/2006 | Gommans ............ | C09D 183/04 524/588 |
| 2015/0374884 | A1 | 12/2015 | Goodrich et al. | |
| 2016/0024239 | A1 | 1/2016 | Goodrich et al. | |
| 2018/0126045 | A1 | 5/2018 | Goodrich | |

OTHER PUBLICATIONS

International Preliminary Report on Patentability (PCT/US2017/064262) issued on Jun. 13, 2019.

Aldenhoff et al (2002) "Stability of radiopaque iodine-containing biomaterials," Biomaterials 23(3):881-886.

Benzina et al (1994) "Studies on a new radiopaque polymeric biomaterial," Biomaterials 15(14):1122-1128.

Benzina et al (1996) "A versatile three-iodine molecular building block leading to new radiopaque polymeric biomaterials," J Biomed Mater Res 32(3):459-466.

International Search Report and Written Opinion issued on Mar. 16, 2018 in PCT/US2017/064262.

Kruft et al. (1994) "Studies on two new radiopaque polymeric biomaterials," J Biomed Mater Res 28: 1259-1266.

Lendlein & Langer (2002) "Biodegradable, elastic shape-memory polymers for potential biomedical applications." Science 296: 1673-1676.

Moszner et al (1995) "Synthesis and polymerization of hydrophobic iodine-containing methacrylates" Die Angewandte Makromolekulare Chemie 224: 115-123.

Novelline (1997) Squire's Fundamentals of Radiology. Harvard University Press. 5th edition. p. 143.

* cited by examiner

RADIOPAQUE POLYMERS WITH ENHANCED RADIOPACITY

CROSS-REFERENCE TO RELATED APPLICATIONS

This application is a National Stage Application filed under 35 U.S.C. 371 of International Application No. PCT/US2017/064262, filed Dec. 1, 2017, which claims the benefit of priority from U.S. Provisional Patent Application No. 62/429,433, filed Dec. 2, 2016, each of which are incorporated herein by reference in their entireties to the extent they are non-inconsistent therewith.

BACKGROUND OF INVENTION

For medical devices used within the body, either permanent implants or instrumentation used for diagnostic or therapeutic purposes, the ability to visualize the device using typical clinical imaging modalities, e.g. X-ray, Fluoroscopy, CT Scan, and MRI is typically a requirement for clinical use. Devices intended to be imaged by X-ray and Fluoroscopy, typically contain either metals or metal byproducts to induce radiopacity. Radiopacity refers to the relative inability of electromagnetism, particularly X-rays, to pass through dense materials, which are described as 'radiopaque' appearing opaque/white in a radiographic image. A more radiopaque material appears brighter, whiter, on the image. (Novelline, Robert. Squire's Fundamentals of Radiology. Harvard University Press. 5th edition. 1997.) Given the complexity of the content within an X-ray or Fluoroscopic image, clinicians are sensitive to the quality of the image regarding the brightness or signal strength of the material in the image. The two main factors that contribute to radiopacity brightness, or signal strength of a material are density and atomic number. Polymer based medical devices requiring radiopacity typically utilize a polymer blend that incorporates a small amount, by weight percent, of a heavy atom, radiopaque filler such as Titanium Dioxide ($TiO_2$), or Barium Sulfate ($BaSO_4$). The device's ability to be visualized on fluoroscopy is dependent upon the amount, or density, of the filler mixed into the material, which is typically limited to a small quantity as the filler can detrimentally affect the base polymer's material properties. Meanwhile, medical device imaging companies have developed standardized liquid contrast media to be intermittently used by physicians to highlight vascular structures, etc. during X-ray or Fluoroscopy when filled with this contrast media. This media commonly contains a heavy atom fluid, such as iodine, to induce radiopacity.

Iodine-incorporating monomers were reported by Mosner et al., who reported 3 different triiodinated aromatic monomers, which differed in the degree to which they could be homopolymerized or required copolymerization in order to be incorporated. (Moszner et al "Synthesis and polymerization of hydrophobic iodine-containing methacrylates" Die Angewandte Makromolekulare Chemie 224 (1995) 115-123) Iodinating monomers were also pursued by Koole et al in the Netherlands, as published from 1994-1996 with a range of monoiodinated to triiodinated aromatic monomers (Koole et al "Studies on a new radiopaque polymeric biomaterial," Biomaterials 1994 November; 15(14):1122-8. Koole et al "A versatile three-iodine molecular building block leading to new radiopaque polymeric biomaterials," J Biomed Mater Res, 1996 November; 32(3):459-66). This included biocompatibility results of a 2-year implantation study in rats of monoiodinated aromatic methacrylate copolymer systems. (Koole et al "Stability of radiopaque iodine-containing biomaterials," Biomaterials 2002 February; 23(3):881-6) They are also discussed by Koole in U.S. Pat. No. 6,040,408, filed initially as a European patent application in August, 1994, which limits its claims to aromatic monomers containing no more than two covalently bonded iodine groups. (U.S. Pat. No. 6,040,408, "Radiopaque Polymers and Methods for Preparation Thereof," Koole, 21 Mar. 2000). Also, US Patent Application 20060024266 by Brandom et al. claimed polyiodinated aromatic monomers in shape memory polymers, emphasizing the use of crystallizable polymer side-groups (US Patent Application 20060024266, "Side-chain crystallizable polymers for medical applications, Brandom et al, 5 Jul. 2005).

U.S. Pat. No. 9,062,141 and U.S. Patent Application Publications 2015/0374884 and 2016/0024239 describe radiopaque compositions having crosslinked monomers. Both of these applications are hereby incorporated by reference in their entirety.

Materials and devices with higher radiopacity are beneficial because they allow for smaller medical devices that can still be detected by imaging techniques. Smaller devices allow for less intrusive procedures and applications in more sensitive areas of a patient's body and safer than their larger counterparts.

It can be seen from the foregoing that there is a need in the art for materials having enhanced useful properties, including higher radiopacity. Higher radiopaque materials allow for the imaging of biomaterial implants with smaller sizes and thicknesses which are detectable using standard clinical imaging modalities.

SUMMARY OF THE INVENTION

Provided generally are radiopaque polymers, compositions or materials that have useful radiopacity properties. Useful radiopacity properties include enhanced radiopacity. As used herein, "enhanced radiopacity" is not intended to reflect a particular numerical value or absolute measure of radiopacity, but rather refers to a composition having a radiopacity quality that is useful for the desired purpose. In one aspect, enhanced radiopacity is useful for imaging the polymers described herein and devices incorporating the polymers described herein. In one aspect, enhanced radiopacity is useful for allowing the polymers described herein to be formulated into materials and devices having desirable properties, including smaller size and/or narrower thickness, than materials and devices that do not use the polymers described herein.

In an aspect, provided is a crosslinked polymer network comprising: a) a plurality of first repeating units derived from a first reagent, the first reagent defined by the formula FX1a, FX1b, FX1c or FX1d:

[FX1a]

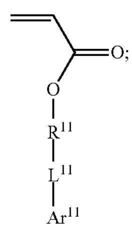

-continued

[FX1b]

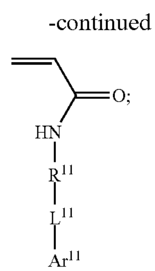

[FX1c]

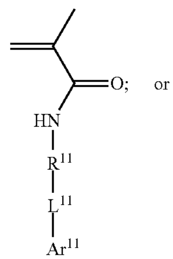

or

[FX1d]

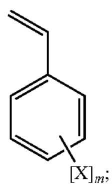

wherein X is Br or I; m is an integer selected from the range of 1 to 5; each $R^{11}$ is independently a substituted or unsubstituted $C_6$-$C_{20}$ alkylene group; each $L^{11}$ is independently a single bond; —$(CH_2)_j$—; —$(HCCH)_j$—; —O—; —S—; —SO—; —$SO_2$—; —$SO_3$—; —$OSO_2$—; —$NR^{12}$—; —CO—; —COO—; —OCO—; —OCOO—; —$CONR^{13}$—; —$NR^{14}CO$—; —$OCONR^{15}$—, —$NR^{16}COO$—, —$NR^{17}CONR^{18}$—; —$SiO(Z^1)(Z^2)$—; or —$Si[SiO(Z^1)(Z^2)]_n$—; wherein $Z^1$ is given by the formula $L^1(T^1)_p$ and $Z^2$ is given by the formula $L^2(T^2)_q$; wherein each of $L^1$ and $L^2$ are independently a single bond, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms and including —O— or —C(O)O—, each of $T^1$ and $T^2$ are independently a polymerizable group having a terminal (meth)acrylate, (meth)acrylamide or styryl group, and n is an integer selected from the range of 1-10; each $Ar^{11}$ is independently an iodine- or bromine-containing $C_5$-$C_{36}$ aryl group containing one or more rings, or an iodine- or bromine-containing $C_5$-$C_{36}$ heteroaryl group containing one or more rings; each of $R^{12}$-$R^{18}$ is independently hydrogen or a $C_1$-$C_{10}$ alkyl group; each j is independently an integer selected from the range of 1 to 10;

b) a plurality of second repeating units derived from a second reagent, the second reagent defined by the formula $Z^3{}_aX^1{}_cSi_dO_eZ^4{}_b$; wherein $Z^3$ is given by the formula $L^3(T^4)_p$ and $Z^4$ is given by the formula $L^4(T^4)_q$; wherein each of $L^3$ and $L^4$ are independently a single bond, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms and including —O— or —C(O)O—, each of $T^3$ and $T^4$ are independently a polymerizable group having a terminal (meth)acrylate, (meth)acrylamide or styryl group; each $X^1$ is independently an alkyl group, a (meth)acrylate group, a (meth)acrylamide group or a styryl group, each group independently having 1 to 36 carbon atoms, 1 to 12 carbon atoms or, optionally, 1 to 20 carbon atoms; wherein each a, b and d are independently integers selected from the range of 1 to 10 and each c and e are independently integers selected from the range of 1 to 20; and wherein p and q are each independently an integer selected from the range of 1 to 9; and c) a plurality of third repeating units derived from a third reagent, the third reagent comprising at least three terminal (meth)acrylate, (meth)acrylamide or styryl groups. In an embodiment, the first reagent, the second reagent and the third reagent are each independently monomers. In embodiments, for example, each third reagent comprises at least three terminal (meth)acrylate, (meth)acrylamide or styryl groups having 2 to 36 carbons, or optionally, 2 to 10 carbons. In embodiments, each $T^1$, $T^2$, $T^3$ and $T^4$ are independently a polymerizable group having a terminal (meth)acrylate, (meth)acrylamide or styryl group having 2 to 36 carbons, 2 to 10 carbons, or optionally, 2 to 3 carbons.

In an embodiment, each $L^{11}$ is independently a single bond; —$(CH_2)_q$—; —$(HCCH)_q$—; —O—; —S—; —SO—; —$SO_2$—; —$SO_3$—; —$OSO_2$—; —$NR^{12}$—; —CO—; —COO—; —OCO—; —OCOO—; —$CONR^{13}$—; —$NR^{14}CO$—; —$OCONR^{15}$—, —$NR^{16}COO$—, or —$NR^{17}CONR^{18}$—. In an embodiment, each $L^{11}$ is independently a single bond; —$(CH_2)_q$—; or —$(HCCH)_q$—;

In embodiments, $Ar^{11}$ is an iodine containing $C_6$ aryl group with 3 to 5 iodine atoms attached directly to the ring. In an embodiment, for example, $R^{11}$ is a $C_6$-$C_{24}$ alkylene group. In some embodiments, the first reagent is defined by the formula FX2:

[FX2]

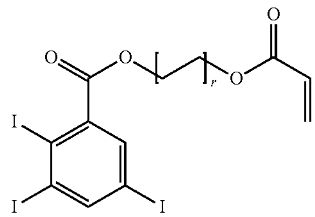

wherein r is an integer selected from the range of 3 to 10. In further embodiments, r is an integer selected from the range of 3 to 8 or 4 to 6. In further embodiments, r is an integer equal to or greater than 6. In further embodiments, r is an integer selected from the range of 6 to 16.

In some embodiments, the third reagent is defined by the formula FX3:

[FX3]

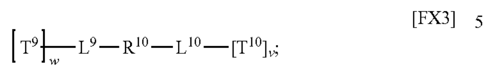

wherein $R^{10}$ is C, N, O, a substituted or unsubstituted $C_2$-$C_{36}$ multivalent alkane radical or a substituted or unsubstituted $C_2$-$C_{36}$ alkylene; each of $L^9$ and $L^{10}$ are independently a single bond, a polyvalent straight or branched $C_2$-$C_{12}$ alkane radical, a polyvalent straight or branched $C_2$-$C_{12}$ heteroalkane radical including-O— or —C(O)O—, $—(CH_2)_n—$, $—(HCCH)_n—$, —O—, —S—, —SO—, $—SO_2—$, $—SO_3—$, $—OSO_2—$, $—NR^3—$, —CO—, —COO—, —OCO—, —OCOO—, $—CONR^4—$, $—NR^5CO—$, $—OCONR^6—$, $—NR^7COO—$, or $—NR^8CONR^9$ and each of $R^3$-$R^9$ is independently hydrogen or $C_1$-$C_{10}$ alkyl and each n is independently an integer selected from 1 to 10; each $T^9$ and each $T^{10}$ are independently a polymerizable group having a terminal (meth)acrylate, (meth)acrylamide or styryl group; and w and v are each independently integers from 1 to 9. In embodiments, the third reagent is a polyamide, a polyether or a polyurethane. In embodiments, each $T^9$ and $T^{10}$ are independently a polymerizable group having a terminal (meth)acrylate, (meth)acrylamide or styryl group having 2 to 36 carbons, 2 to 10 carbons, or optionally, 2 to 3 carbons.

In some embodiments, for example, $R^{10}$ is O; $L^9$ and $L^{10}$ are each a branched tetravalent pentane radical, the total number of terminal groups is 6 with from 1 to 6 terminal groups being defined by the formula FX6:

[FX6]

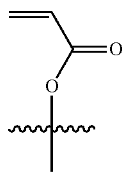

and the balance of the terminal groups being —OH. In embodiments, the crosslinking monomer having three or more polymerizable groups is dipentaerythritol pentaacrylate ([2-(hydroxymethyl)-3-prop-2-enoyloxy-2-[[3-prop-2-enoyloxy-2,2-bis(prop-2-enoyloxymethyl) propoxy]methyl]propyl] prop-2-enoate), dipentaerythritol hexaacrylate; dipentaerythritol triacrylate; dipentaerythritol tetraacylate In additional embodiments, $R^{10}$ is defined by the formula FX4a, FX4b, FX4c or FX4d:

[FX4a]

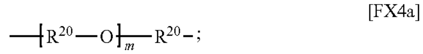

[FX4b]

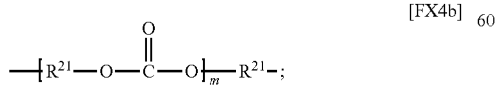

[FX4c]

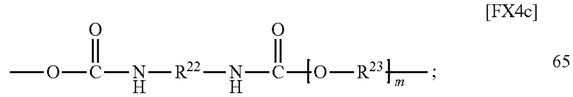

-continued

[FX4d]

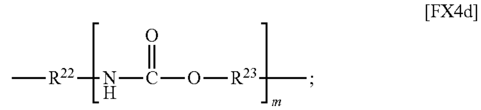

wherein $R^{20}$ is a $C_4$-$C_{20}$ alkylene, $R^{21}$ is a $C_3$-$C_{20}$ alkylene, $R^{22}$ is an divalent aliphatic group, substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, divalent aromatic group, divalent polyalkyl, divalent polyaromatic or mixed aromatic-aliphatic siloxane group, divalent polyether group, divalent polyester group, divalent polycarbonate group or a combination of linear or branched divalent aliphatic groups and divalent aromatic groups, $R^{23}$ is a divalent aliphatic group, substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, divalent aromatic group, divalent polyalkyl, divalent polyaromatic group, divalent mixed aromatic-aliphatic siloxane group, divalent polyether group, divalent polyester group, divalent polycarbonate group or a combination of linear or branched a divalent aliphatic groups and divalent aromatic groups and m is an integer from 1 to 50.

In an embodiment, the second reagent is a siloxane-based crosslinker including, for example, a siloxane or polysiloxane with at least two terminal polymerizable groups. In some embodiments, the siloxane-based crosslinker is branched to allow for additional terminal polymerizable, for example, 3, 4, 5, 6, 7, or 8 terminal polymerizable groups. Branching may occur from the siloxane group or from other groups such as linking groups between the siloxane and the terminal polymerizable groups. Examples of terminal polymerizable groups include (meth)acrylate, (meth)acrylamide or styryl groups.

In some embodiments, the second reagent is given by FX5a

[FX5a]

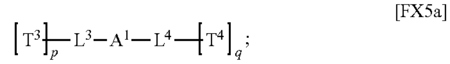

wherein $A^1$ is Si or is defined by the formula FX5b, FX5c, FX5d, FX5e or FX5f:

[FX5b]

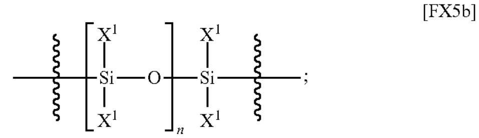

[FX5c]

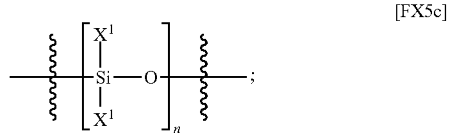

-continued

[FX5d]

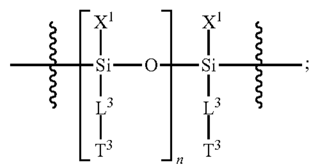

[FX5e]

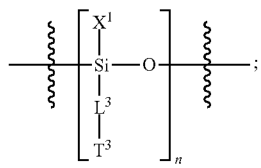

[FX5f]

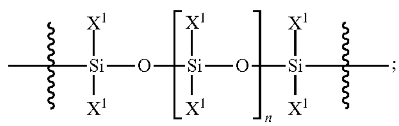

each $X^1$ is independently an alkyl group, a (meth)acrylate group, a (meth)acrylamide group or a styryl group, each group independently having 1 to 36 carbon atoms, 1 to 12 carbon atoms or, optionally, 1 to 20 carbon atoms, atoms, n is from 1 to 10, each of p and q are independently integers from 1 to 9, each $L^3$ and $L^4$ is independently a single bond, C, N, O, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms, and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms and including —O— or —C(O)O—, a straight or branched $C_2$-$C_{12}$ alkylene group; a straight or branched $C_2$-$C_{12}$ oxyalkylene group; a straight or branched $C_2$-$C_{12}$ carboxyalkylene group; a straight or branched $C_2$-$C_{12}$ oxyarylene group or a straight or branched $C_2$-$C_{12}$ carboxyarylene group and each $T^3$ and $T^4$ is independently a polymerizable group having a terminal(meth)acrylate, (meth)acrylamide or styryl group.

In an embodiment, for example, the second reagent is defined by the formula FX5g:

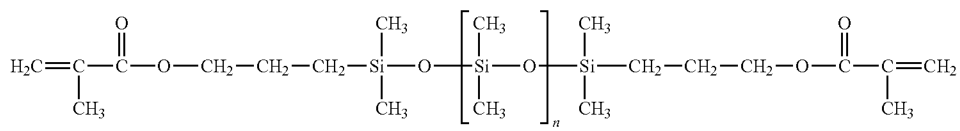

[FX5g]; wherein n selected from the range of 1 to 10, 1 to 5, or optionally, 1 to 2.

As an example, $A^1$ is $(SiMe_2\text{-}O)_x$—$SiMe_2$ where Me is a methyl group, $L^3$ and $L^4$ each are a polyvalent straight or branched $C_2$-$C_{12}$ alkane radical and $T^3$ and $T^4$ each are —O—C(O)—CH═$CH_2$ or —O—C(O)—CMe═$CH_2$. As another example, $A^1$ is $(Si\ Me_2\text{-}O)_x$—$SiMe_2$ where Me is a methyl group, $L^3$ and $L^4$ each are a single bond and $T^3$ and $T^4$ each are (—O—C(O)—CH═$CH_2$), forming the structure $CH_2$═CH—C(O)—O—$(Si\ Me_2\text{-}O)_x$—$SiMe_2$-O—C(O)—CH═$CH_2$. As another example, $A^1$ is $(Si\ Me_2\text{-}O)_x$—$SiMe_2$ where Me is a methyl group, $L^3$ and $L^4$ each are a single bond and $T^3$ and $T^4$ each are (—O—C(O)—CMe═$CH_2$), forming the structure $CH_2$═CMe-C(O)—O—$(Si\ Me_2\text{-}O)_x$—$SiMe_2$-O—C(O)—CMe═$CH_2$. In addition, Si molecules may be bonded directly to polymerizable groups, (for example, (meth)acrylate, (meth)acrylamide) or styryl groups), to a linking group bonded to a polymerizable group or other groups as described herein.

Some commercial examples of useful reagents for crosslinking include, for example: U.S. Pat. No. 5,162,396 (Dow Corning), see Formula II:

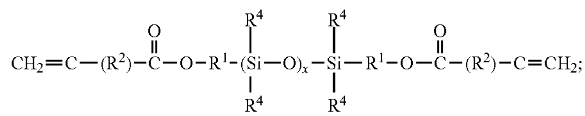

From U.S. Pat. No. 6,160,148 (Wacker Chemie, "Organosilicon Compounds Containing (Meth)Acrylate Groups . . . ") see Formula I and Example I

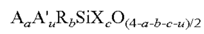 Formula I

From Example I: Q-SiMe2O(SiMe2O)54-SiMe2-Q.

As well as commercially available Sigma-Aldrich™ reagents including:

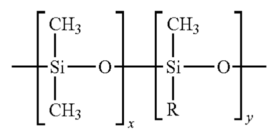

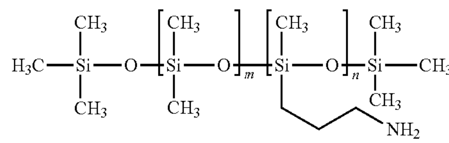

or (Methacryloxypropyl)methylsiloxane or (Acryloxypropyl)methylsiloxane):

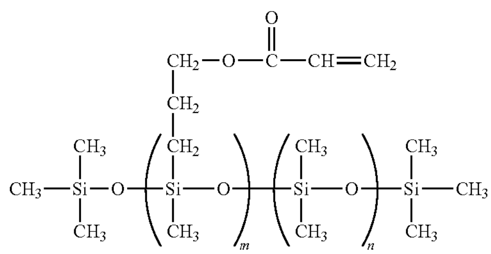

In embodiments, the crosslinked polymer network has greater than or equal to 15 wt % of repeating units from the first reagent, greater than or equal to 50 wt % of repeating units from the first reagent or, for example, greater than or equal to 85 wt % of repeating units from the first reagent. In an embodiment, the crosslinked polymer network has greater than or equal to 50 wt % and less than or equal to 85 wt % of repeating units from the first reagent.

In embodiments, the crosslinked polymer network has less than or equal to 85 wt % of repeating units from the second reagent, less than or equal to 50 wt % of repeating units from the second reagent or, for example, less than or equal to 15 wt % of repeating units from the second reagent or, for example, less than or equal to 5 wt % of repeating units from the second reagent. In an embodiment, the crosslinked polymer network has less than or equal 50 wt % and greater than or equal to 20 wt % of repeating units from the second reagent, or for some embodiments, the crosslinked polymer network has less than or equal 5 wt % and greater than or equal to 2 wt % of repeating units from the second reagent. In an embodiment, for example, the crosslinked polymer network has 3 wt % to 5 wt % repeating units from the second reagent.

In embodiments, the crosslinked polymer network has less than or equal to 85 wt % of repeating units from the third reagent, less than or equal to 50 wt % of repeating units from the third reagent or, for example, less than or equal to 10 wt % of repeating units from the third reagent. In an embodiment, the crosslinked polymer network has less than or equal to 50 wt % and greater than or equal to 20 wt % of repeating units from the third reagent.

In an embodiment for example, the crosslinked polymer network comprises between 80 to 90 wt % of repeating units from the first reagent, 1 to 10 wt % of repeating units from the second reagent and 5 to 15 wt % of repeating units from the third reagent.

In further embodiments, one or more additional reagents, such as an additional crosslinker monomer or a monofunctional monomer, are present in the composition. Exemplary crosslinker molecules include those with three or more polymerizable groups and molecules with two polymerizable groups.

In an aspect, provided is a polymer device for medical application, the device feature comprising a polymer composition as described herein. In an embodiment, the device is for the purpose of an indwelling, permanent implant to provide the function of: i) opening, or maintaining an open anatomical lumen; or ii) closing an anatomical lumen, either partially as a valve, or complete lumen occlusion for any physiological fluid or gas flow or for an applied therapeutic fluid or gas flow; or iii) support of an anatomical structure to assist in therapeutic restoration of an organ, vascular, digestive, excrement, or airway function; or iv) support of an anatomical structure to assist in therapeutic restoration of an orthopedic, maxiofacial, spinal, joint or other skeletal or function; or v) to support hemostasis by covering an area after tissue dissection or resection.

In embodiments, for example, the device or device feature comprises a fiber, a coil or a mesh. In embodiments, for example, the device is for the purposes of a diagnostic or therapeutic instrument or device to provide the function of: a catheter for the purposes of accessing an anatomical location; delivering another device and/or therapeutic agent; or controlling the access or delivery of another device and/or therapeutic agent; or a temporarily indwelling device to provide a limited time therapeutic benefit-left indwelling for a period of time—and subsequently removed when the therapeutic period is completed.

In embodiments, the device or a portion of the device has a cylindrical shape with a diameter less than or equal to 0.020 inches, less than or equal to 0.015 inches, less than or equal to 0.012 inches or, for example, less than or equal to 0.010 inches.

In an aspect, provided is a method for making a crosslinked polymer composition comprising the steps of: a) forming a polymer precursor mixture comprising: i) a first reagent defined by the formula FX1a, FX1b, FX1c or FX1d:

[FX1a]

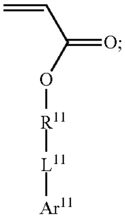

[FX1b]

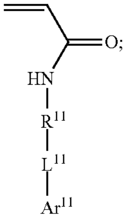

[FX1c]

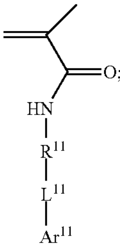

or

[FX1d]

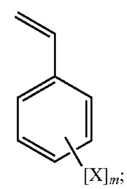

wherein X is Br or I; m is an integer selected from the range of 1 to 5; each $R^{11}$ is independently a substituted or unsubstituted $C_6$-$C_{20}$ alkylene group; each $L^{11}$ is independently a single bond; —$(CH_2)_j$—; —$(HCCH)_j$—; —O—; —S—; —SO—; —$SO_2$—; —$SO_3$; —$OSO_2$—; —$NR^{12}$—; —CO—; —COO—; —OCO—; —OCOO—; —$CONR^{13}$—; —$NR^{14}CO$—; —$OCONR^{15}$—, —$NR^{16}COO$—, —$NR^{17}CONR^{18}$—, —$SiO(Z^1)(Z^2)$—; or —$Si[SiO(Z^1)(Z^2)]_n$—; wherein $Z^1$ is given by the formula $L^1(T^1)_p$ and $Z^2$ is given by the formula $L^2(T^2)_q$; wherein each of $L^1$ and $L^2$ are independently a single bond, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms and including —O— or —C(O)O—, each of $T^1$ and $T^2$ are independently a polymerizable group having a terminal (meth)acrylate, (meth)acrylamide or styryl group, and n is an integer selected from the range of 1-10; each $Ar^{11}$ is independently an iodine- or bromine-containing $C_5$-$C_{36}$ aryl group containing one or more rings, or an iodine- or bromine-containing $C_5$-$C_{36}$ heteroaryl group containing one or more rings; each of $R^{12}$-$R^{18}$ is independently hydrogen or a $C_1$-$C_{10}$ alkyl group; each j is independently an integer selected from the range of 1 to 10;

ii) a second reagent defined by the formula $Z^3{}_aX^1{}_cSi_dO_eZ^4{}_b$; wherein $Z^3$ is given by the formula $L^3(T^3)_p$ and $Z^4$ is given by the formula $L^4(T^4)_q$; wherein each of $L^3$ and $L^4$ are independently a single bond, a polyvalent alkane radical having from 1 to 36 carbon atoms, a polyvalent heteroalkane radical having from 1 to 36 carbon atoms and including —O— or —C(O)O—, a polyvalent aryl radical having from 1 to 36 carbon atoms, or a polyvalent heteroaryl radical having from 1 to 36 carbon atoms and including —O— or —C(O)O—, each of $T^3$ and $T^4$ are independently a polymerizable group having a terminal (meth)acrylate, (meth) acrylamide or styryl group; each $X^1$ is independently an alkyl group, a (meth)acrylate group, a (meth)acrylamide group or a styryl group, each group independently having 1 to 36 carbon atoms; wherein each a, b and d are independently integers selected from the range of 1 to 10 and each c and e are independently integers selected from the range of 1 to 20; and wherein p and q are each independently an integer selected from the range of 1 to 9; and iii) a third reagent comprising at least three terminal (meth)acrylate, (meth)acrylamide or styryl groups;

b) polymerizing the polymer precursor mixture with an initiator. In an embodiment, the first reagent, the second reagent and the third reagent are each independently monomers. In embodiments, for example, each third reagent comprises at least three terminal (meth)acrylate, (meth) acrylamide or styryl groups having 2 to 36 carbons, or optionally, 2 to 10 carbons. In embodiments, each $T^1$, $T^2$, $T^3$ and $T^4$ are independently a polymerizable group having a terminal (meth)acrylate, (meth)acrylamide or styryl group having 2 to 36 carbons, 2 to 10 carbons, or optionally, 2 to 3 carbons.

In embodiments, the crosslinked polymer network has less than or equal to 85 wt % of the second reagent, less than or equal to 50 wt % of the second reagent or, for example, less than or equal to 15 wt % of the second reagent. In an embodiment, the crosslinked polymer network has less than or equal 50 wt % and greater than or equal to 20 wt % of the second reagent.

In embodiments, the crosslinked polymer network has less than or equal to 85 wt % of the third reagent, less than or equal to 50 wt % of the third reagent or, for example, less than or equal to 10 wt % of the third reagent. In an embodiment, the crosslinked polymer network has less than or equal to 50 wt % and greater than or equal to 20 wt % of the third reagent.

In an embodiment for example, the crosslinked polymer network comprises between 80 to 90 wt % of the first reagent, 1 to 10 wt % of the second reagent, and 5 to 15 wt % of the third reagent.

In embodiments, the second reagent is defined by the formula FX5a:

[FX5a]

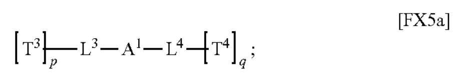

wherein $A^1$ is Si or is defined by the formula FX5b, FX5c, FX5d, FX5e or FX5f:

[FX5b]

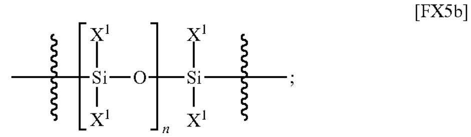

[FX5c]

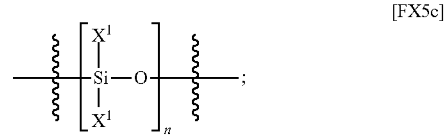

[FX5d]

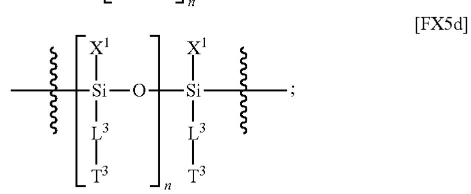

[FX5e]

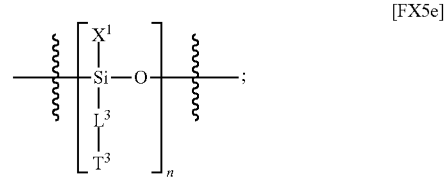

[FX5f]

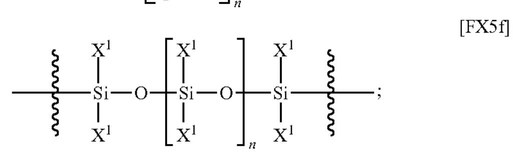

each $X^1$ is independently an alkyl group, a (meth)acrylate group, a (meth)acrylamide group or a styryl group, each group independently having 1 to 36 carbon atoms, n is from 1 to 10, each of p and q are independently integers from 1 to 9, each $L^3$ and $L^4$ is independently a single bond, C, N, O, a polyvalent alkane radical having from 1 to 36 carbon atoms, a polyvalent heteroalkane radical having from 1 to 36 carbon atoms and including —O— or —C(O)O—, a polyvalent aryl radical having from 1 to 36 carbon atoms, or a polyvalent heteroaryl radical having from 1 to 36 carbon atoms and including —O— or —C(O)O—, a straight or branched $C_2$-$C_{12}$ alkylene group; a straight or branched $C_2$-$C_{12}$ oxyalkylene group; a straight or branched $C_2$-$C_{12}$ carboxyalkylene group; a straight or branched $C_2$-$C_{12}$ oxyarylene group or a straight or branched $C_2$-$C_{12}$ carboxyarylene group and each $T^3$ and $T^4$ is independently a polymerizable group having a terminal(meth)acrylate, (meth)acrylamide or styryl group.

In an embodiment, for example, the second reagent is defined by the formula FX5g:

[FX5g]

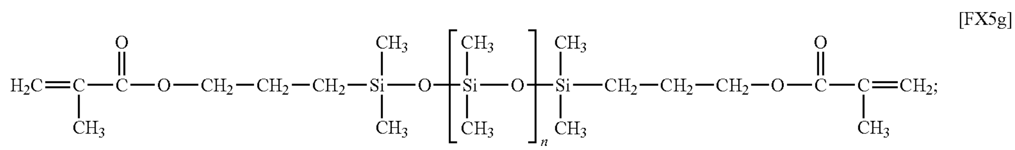

wherein n selected from the range of 1 to 10, 1 to 5, or optionally, 1 to 2.

In an embodiment, the first regent is defined by the formula FX2:

[FX2]

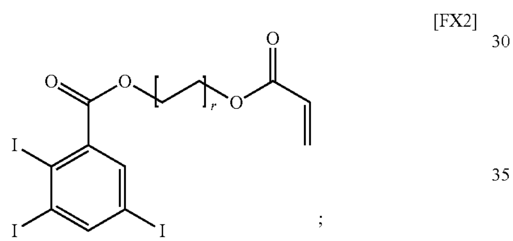

wherein r is an integer selected from the range of 2 to 18.

In an aspect, provided is a crosslinked polymer network comprising:

a) a plurality of first repeating units derived from a first reagent, the first reagent defined by the formula FX1a, FX1b, FX1c or FX1d:

[FX1a]

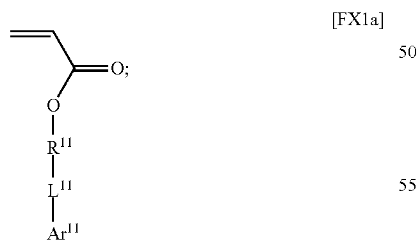

[FX1b]

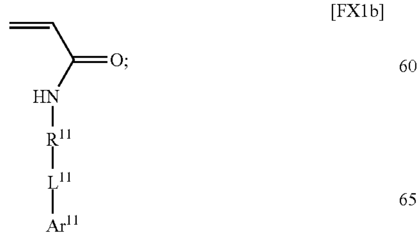

-continued

[FX1c]

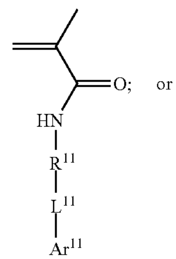

or

[FX1d]

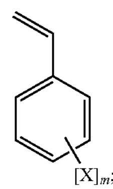

wherein X is Br or I; m is an integer selected from the range of 1 to 5; each $R^{11}$ is independently a substituted or unsubstituted $C_6$-$C_{20}$ alkylene group; each $L^{11}$ is independently a single bond; $—(CH_2)_j—$; $—(HCCH)_j—$; —O—; —S—; —SO—; $—SO_2—$; $—SO_3—$; $—OSO_2—$; $—NR^{12}—$; —CO—; —COO—; —OCO—; —OCOO—; $—CONR^{13}—$; $—NR^{14}CO—$; $—OCONR^{16}—$, $—NR^{16}COO—$, $—NR^{17}CONR^{18}—$, $—SiO(Z^1)(Z^2)—$; or $—Si[SiO(Z^1)(Z^2)]_n—$; wherein $Z^1$ is given by the formula $L^1(T^1)_p$ and $Z^2$ is given by the formula $L^2(T^2)_q$; wherein each of $L^1$ and $L^2$ are independently a single bond, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms and including —O— or —C(O)O—, each of $T^1$ and $T^2$ are independently a polymerizable group having a terminal (meth)acrylate, (meth)acrylamide or styryl group, and n is an integer selected from the range of 1-10; each $Ar^{11}$ is independently an iodine- or bromine-containing $C_5$-$C_{36}$ aryl group containing one or more rings, or an iodine- or bromine-containing $C_5$-$C_{36}$ heteroaryl group containing one or more rings; each of $R^{12}$-$R^{18}$ is independently hydrogen or a $C_1$-$C_{10}$ alkyl group; each j is independently an integer selected from the range of 1 to 10; and b) a plurality of second repeating units derived from a second reagent, the second reagent defined by the formula $Z^3_aX^1_cSi_dO_eZ^4_b$; wherein $Z^3$ is given by the formula $L^3(T^3)_p$ and $Z^4$ is given by the formula $L^4(T^4)_q$; wherein each of $L^3$ and $L^4$ are independently a single bond, a polyvalent alkane radical having from 1 to 36 carbon atoms, 1 to 12 carbon atoms or, optionally, 1 to 20 carbon atoms, a polyvalent heteroalkane radical having from 1 to 36 carbon atoms, 1 to 12 carbon atoms or, optionally, 1 to 20 carbon atoms, and including —O— or —C(O)O—, a polyvalent aryl radical having from 1 to 36 carbon atoms, 1 to 12 carbon atoms or, optionally, 1 to 20 carbon atoms, or a polyvalent heteroaryl radical having from 1 to 36 carbon atoms, 1 to 12 carbon atoms or, optionally, 1 to 20 carbon atoms, and including —O— or —C(O)O—; each of $T^3$ and $T^4$ are independently a polymerizable group having a terminal (meth)acrylate, (meth)acrylamide or styryl group; each $X^1$ is independently an alkyl group, a (meth)acrylate group, a (meth)acrylamide group or a styryl group, each group independently having 1 to 36 carbon atoms; wherein each a, b and d are independently integers selected from the range of 1 to 10 and each c and e are independently integers selected from the range of 1 to 20; and wherein p and q are each independently an integer selected from the range of 1 to 9. In an embodiment, the first reagent, the second reagent and the third reagent are each independently monomers. In embodiments, for example, each third reagent comprises at least three terminal (meth)acrylate, (meth)acrylamide or styryl groups having 2 to 36 carbons, or optionally, 2 to 10 carbons. In embodiments, each $T^1$, $T^2$, $T^3$ and $T^4$ are independently a polymerizable group having a terminal (meth)acrylate, (meth)acrylamide or styryl group having 2 to 36 carbons, 2 to 10 carbons, or optionally, 2 to 3 carbons.

In embodiments, the crosslinked polymer network has greater than or equal to 15 wt % of repeating units from the first reagent, greater than or equal to 50 wt % of repeating units from the first reagent or, for example, greater than or equal to 85 wt % of repeating units from the first reagent. In an embodiment, the crosslinked polymer network has greater than or equal to 50 wt % and less than or equal to 95 wt % of repeating units from the first reagent.

In embodiments, the crosslinked polymer network has less than or equal to 85 wt % of repeating units from the second reagent, less than or equal to 50 wt % of repeating units from the second reagent or, for example, less than or equal to 15 wt % of repeating units from the second reagent. In an embodiment, the crosslinked polymer network has less than or equal 50 wt % and greater than or equal to 4 wt % of repeating units from the second reagent.

In an embodiment for example, the crosslinked polymer network has a wt % selected from the range of 85 wt % to 97 wt % of the first reagent and a wt % selected from the range of 0.5 wt % to 10 wt % of the second reagent.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
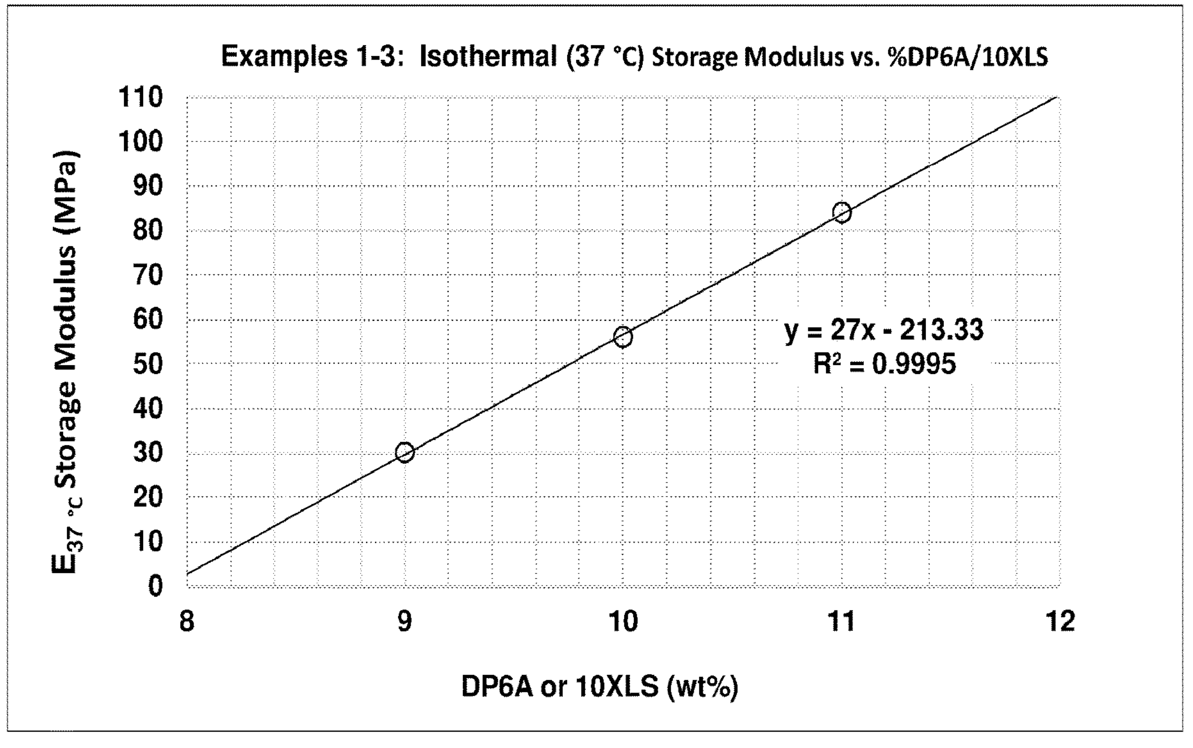
FIG. 1. provides a plot with weight percent of DP6A or 10XLS on the x-axis and storage modulus (MPa at 37° C.) on the y-axis.
Figure 2:
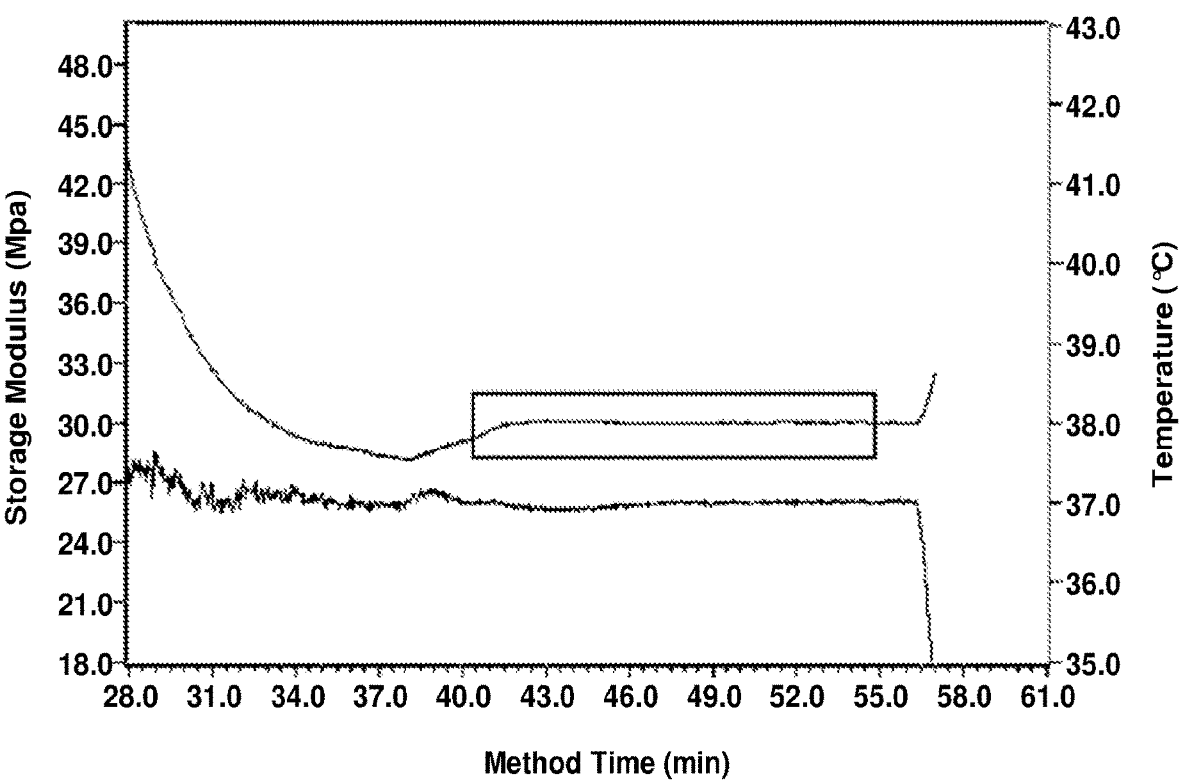
FIG. 2. provides a plot with time on the x-axis and storage modulus and temperature on the y-axis.
Figure 3:
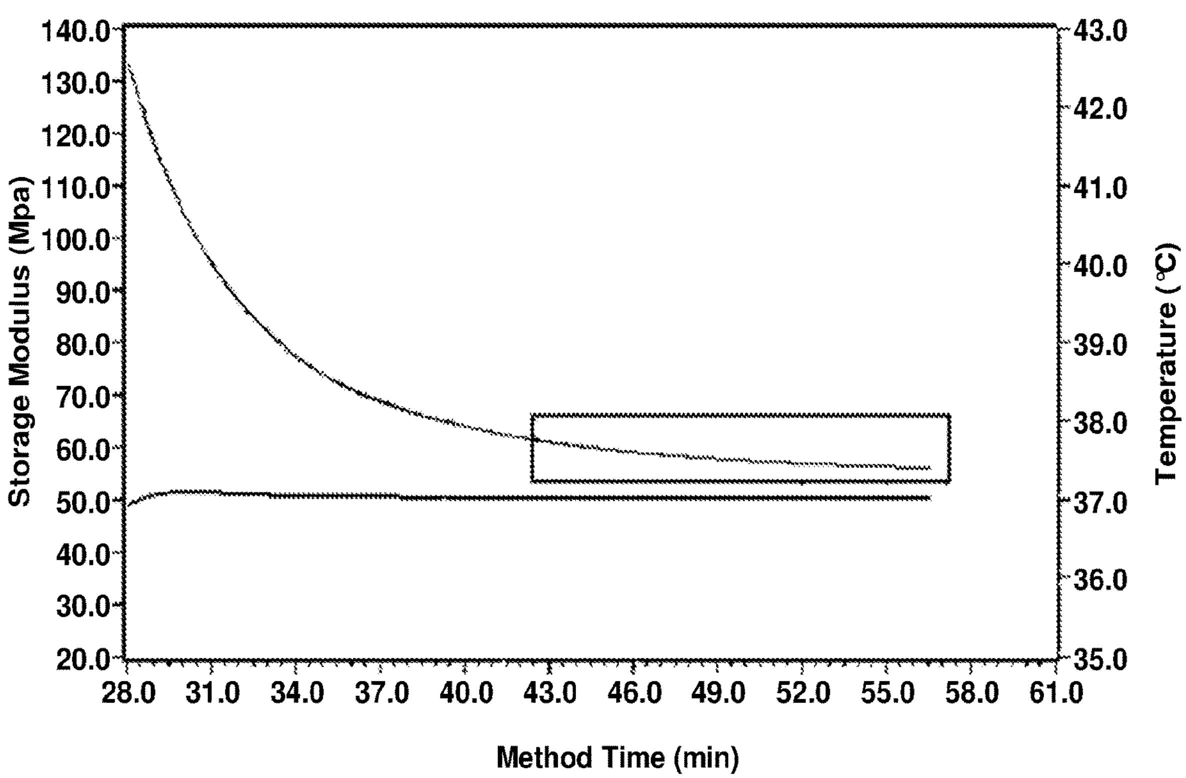
FIG. 3. provides a plot with time on the x-axis and storage modulus and temperature on the y-axis.
Figure 4:
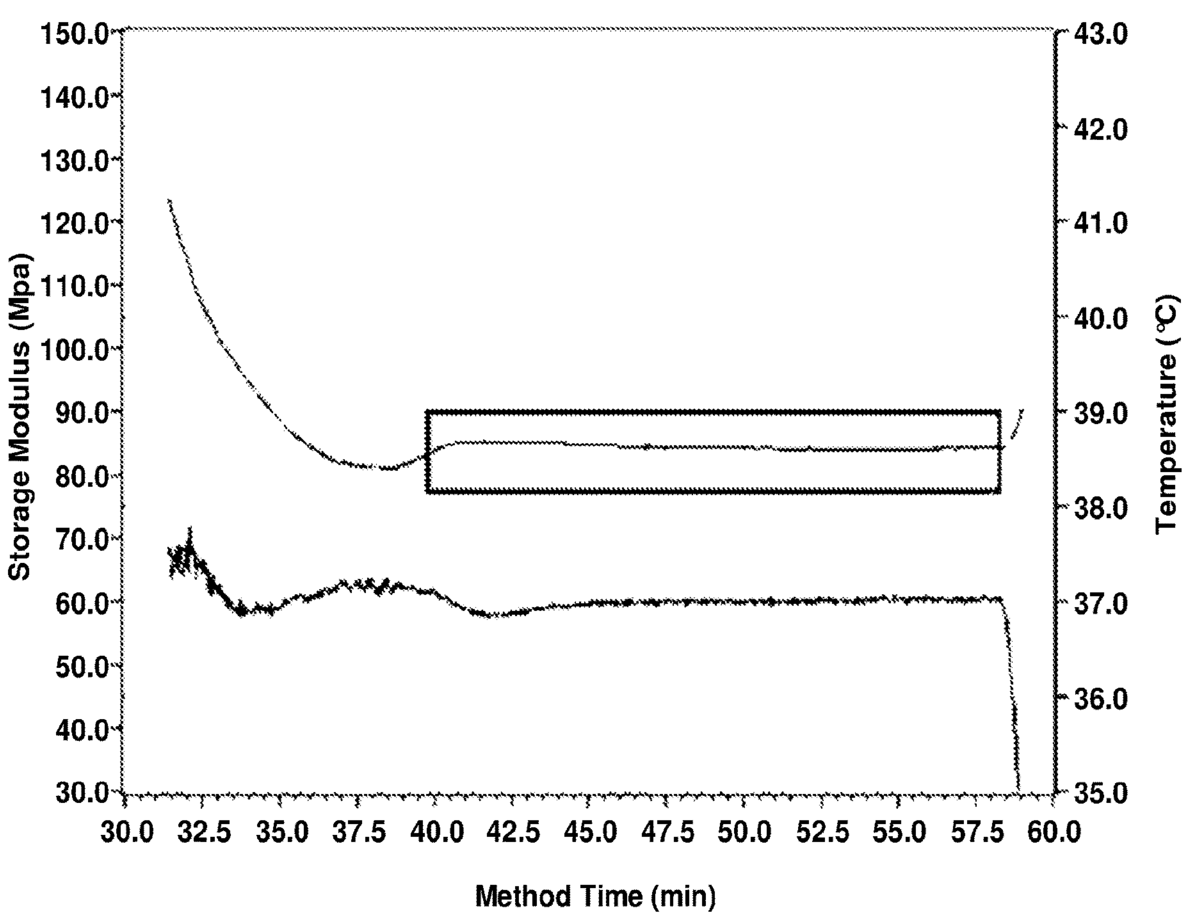
FIG. 4. provides a plot with time on the x-axis and storage modulus and temperature on the y-axis.
Figure 5:
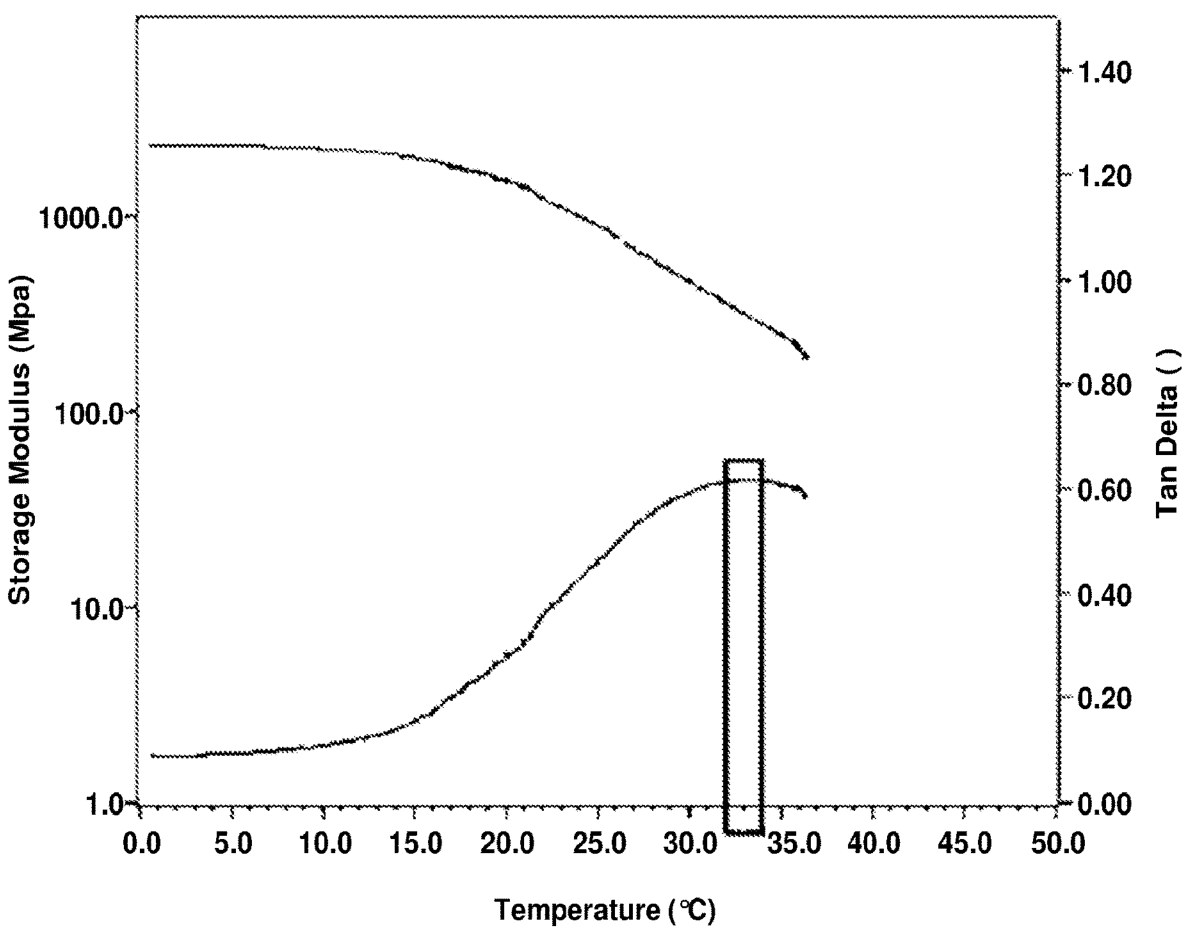
FIG. 5. provides a plot with time on the x-axis and storage modulus and temperature on the y-axis.

In an aspect, provided is a polymer composition obtained by the polymerization of a plurality of reactants, the plurality of reactants comprising a first reactant comprising a radiopaque functionality, a second reactant comprising three or more polymerizable groups and a third reactant comprising according to formula FX2a or FX2b. Additional reactants, such as additional crosslinking reagents, may also be polymerized with the first, second and third reactants. In an embodiment, the polymer composition is crosslinked. The polymer composition comprises a plurality of repeating units derived from each of the reactants. In an embodiment, the first reagent comprises one or more monomers including iodine or bromine and also including a polymerizable group. The second reagent comprises a crosslinking reagent. Crosslinking reagents useful for the present invention include monomers or oligomers which are branched and which comprise at least three terminal polymerizable groups, but which do not comprise iodine or bromine. In an embodiment, the terminal polymerizable groups are located at the ends of branches. The crosslinking monomer or oligomer may comprise at least three (meth)acrylate, (meth)acrylamide or styryl groups. In other embodiments, the monomer or oligomer may comprise from 3 to 20, from 6 to 20 or from 8 to 20 polymerizable groups. The crosslinking monomer or oligomer may further comprise one or more terminal functional groups other than polymerizable groups. For example, the crosslinking monomer or oligomer may further comprise one or more terminal acyl chloride, carboxyl, ester or amide groups.

The crosslinker monomer or oligomer, in combination with the other monomers in the mixture, allows formation of a crosslinked network. The structure and amount of crosslinker(s) in the polymer precursor mixture may be selected to provide a sufficiently high crosslink density to achieve the desired modulus in the composition. In different embodiments, the molecular weight of the crosslinker is in the range from 100 to 1000, 200 to 2000 or 200 to 5000, 2000 to 20,000 or any other useful molecular weight range.

Optionally the crosslinking monomer is a polyamide or a polyether. For example, the polyamide or polyether may be difunctional, such as a diacrylate or dimethacrylate monomer.

Blends of crosslinkers can allow shorter and longer crosslinkers to be used together. In an embodiment, one of the crosslinker monomers or oligomers may be of higher molecular weight than the other(s). In an embodiment, one of the crosslinker monomers or oligomers has a molecular weight greater than or equal to 250 and less than or equal to 1000 and the other has a molecular weight greater than 1000 and less than 5000. In an embodiment, one of the crosslinker molecules has a molecular weight greater than or equal to 500 and less than or equal to 1000 and the other has a molecular weight greater than or equal to 1500 and less than or equal to 3000. In an embodiment, one of the crosslinker monomers or oligomers may have a molecular weight greater than or equal to 200 and less than 500 while the other may have a molecular weight greater than or equal to 500 and less than or equal to 1000.

As used herein, (meth)acrylate may refer to both methacrylate and acrylate in that the methyl group is optional. Similarly, (meth)acrylamide may refer to both methacrylamide and acrylamide.

In an embodiment, a crosslinker monomer or oligomer may be classified as "hydrophobic". In an embodiment, a hydrophobic monomer or oligomer may be defined as being insoluble in water. In an embodiment, the crosslinker monomer or oligomer is less soluble in water than a poly(ethylene glycol) di(meth)acrylate of comparable molecular weight.

An optional monofunctional non-iodinated co-monomer can be used to adjust the properties of the polymer. For example, the co-monomer can be used to modify the glass transition temperature (Tg) of the polymer. As another example, the co-monomer can be selected to assist in system compatibilization.

In an embodiment, the co-monomer is a vinyl monomer. A wide range of commercially-available vinyl monomers can be utilized, including but not limited to butyl acrylate, which imparts a Tg value near −40° C. Such a low glass transition temperature can help to offset the typically higher Tg contribution of radiopaque monomer and crosslinkers having relatively low molecular weight values. The amenability of a wide cross section of vinyl monomers to polymerization or copolymerization by a free radical mechanism facilitates access to useful structure-property modifications.

In an embodiment, the monofunctional co-monomer comprises an acrylate polymerizable group. In another embodiment, the monofunctional co-monomer comprises a styrene, acrylamide, or methacrylamide polymerizable group. In an embodiment, the polymerizable group is an end group. Though styrene monomers typically do not polymerize as aggressively and to as high a conversion as acrylates, in copolymerization reactions with acrylates styrene monomers propagate more readily and can be used to good advantage where required.

A wide range of free radical initiating systems may be used for polymerization. In different embodiments, the initiator may be a photoinitiator, a thermal initiator or a redox (reduction oxidation) initiator. Photoinitiating systems are particularly useful, provided that a photoinitiator is chosen that does not require wavelengths of light that are absorbed excessively by the base monomer ingredients of the formulation. Irgacure 819 (Ciba (BASF), Bis(2,4,6-trimethylbenzoyl)-phenylphosphineoxide) is one example of a photoinitiator that has been found to be particularly useful for the curing system.

Photopolymerization occurs when monomer solution is exposed to light of sufficient power and of a wavelength capable of initiating polymerization. The wavelengths and power of light useful to initiate polymerization depends on the initiator used. Light used in the invention includes any wavelength and power capable of initiating polymerization. Preferred wavelengths of light include ultraviolet. In different embodiments, the light source primarily provides light having a wavelength from 200 to 500 nm or from 200 to 400 nm. In an embodiment, 1-100 $mW/cm^2$ of 200-500 nm light is applied for a time from 10 sec to 60 mins. Any suitable source may be used, including laser sources. The source may be filtered to the desired wavelength band. The source may be broadband or narrowband, or a combination. The light source may provide continuous or pulsed light during the process.

Thermal initiating systems, with low-temperature or high-temperature initiators, common examples being benzoyl peroxide and azobisisobutyronitrile (AIBN), are also useful in situations where a particularly large or irregularly-shaped object that is difficult to illuminate uniformly is to be prepared. Also of use in the latter scenario are free radical initiating systems that produce free radicals by any type of redox reaction, such as the Fenton system involving ferrous salts with tert-butyl hydroperoxide, or other metal-organic, organic such as triethylamine+hydroperoxides, or photo-organic redox systems, an example of the latter being the Eosin-Y+triethanolamine visible light initiating system.

A number of pseudo-living free radical polymerization systems, some of which are capable of producing polymers with narrower molecular weight distributions than conventional free radical polymerizations, are also described in the art and can be amenable to production of crosslinker segments for SMPs or for SMP curing. For example, styrene monomers that polymerize to low conversion in a conventional system may be driven to high conversion in a pseudo-living system. These pseudo-living systems typically involve variable combinations of reversible chain propagation-termination and/or chain transfer steps. "Living" free radical polymerizations known to the art include, but are not limited to, NMP, RAFT, and ATRP.

Additionally; any other type of non-conventional free radical polymerization process, whether pseudo-living or not, that produces free radicals capable of initiating polymerization of the radiopaque and non-radiopaque monomers and crosslinkers comprising the SMPs of this invention, fall within the scope of potential initiating-polymerization methods. These and other free radical initiating systems are conceivable and known to those skilled in the art.

In embodiments, examples of the useful initiating systems include anionic, cationic, free radical polymerizations that are non-living, pseudo-living or living as well as Ziegler-Natta and olefin metathesis. The use of these systems is known in the art. In an embodiment, these systems are useful if a prepolymerized segment is at least difunctional and has hydroxyl or other groups known in the art which can be used to attach polymerizable groups, including acrylate groups in an embodiment.

In an embodiment, some or all of the components of the polymer precursor mixture are combined at a temperature greater than ambient temperature. In different embodiments, the initiator may be added at the same time as the monomer components or added just prior to or at the time of molding. In another embodiment where a thermal initiator is used, the polymer precursor mixture ingredients may be divided into two parts; wherein the high storage temperature ingredients are in Part A, and the lower storage temperature ingredients are in Part B. The thermal initiator may be added to the lower storage temperature ingredients in Part B at a storage temperature that is below the initiator's polymerization temperature. In an embodiment, forming the polymer precursor mixture (or a portion of the polymer precursor mixture) at greater than ambient temperature can assist in maintaining solubility of the polymer precursor mixture components, thereby enabling formation of a homogenous mixture.

In an embodiment, the polymer precursor mixture is held at a temperature greater than ambient temperature during free radical polymerization. In an embodiment, the polymer precursor mixture is held a temperature between 65° C. and 150° C. or from 65° C. and 100° C. during the polymerization step. In an embodiment, a pre-cure step is performed in a vacuum environment. In separate embodiments, the curing step is performed using free radical, anionic, cationic, Diels-alder, thiol-ene, polycondensation, or other mechanisms known in the art. During molding, pressure may be applied during polymerization to ensure mold filling.

In an embodiment, an additional curing or heat treatment step is employed after the polymerization step (e.g. after photopolymerization). In an embodiment, the cured parts are removed from the mold and then undergo additional curing operations through exposure to elevated temperatures. In an embodiment, the curing temperature is from 50° C. and 150° C. and the curing time from 5 seconds to 60 minutes during this additional step.

In different embodiments, the amount of functional group conversion is at least 30%, 40%, 50%, 60%, 70%, 80% or 90% or higher. In an embodiment, the amount of extractables is less than or equal to 1% or less than or equal to 0.5%. In an embodiment, the amount of extractables is less than or equal to 5%. In an embodiment, the amount of extractables is less than or equal to 3%. In an embodiment, the amount of extractables is less than or equal to 2%. In an embodiment, the amount of extractables is determined by isopropanol extraction.

As used herein, a crystalline material displays long range order. The crystallinity of polymers is characterized by their degree of crystallinity, or weight or volume fraction of crystalline material in the sample ranging from zero for a completely non-crystalline polymer to one for a theoretical completely crystalline polymer.

If a polymer is semicrystalline, shape change can be hindered and slowed, and performance of devices incorporating the polymer can become clinically unacceptable. In an embodiment, the polymer compositions of the invention are considered substantially amorphous. As used herein, substantially amorphous is defined as the absence of crystalline features as detected by differential scanning calorimetry (DSC), or by inconsistency and lack of reproducibility in mechanical tensile test results, e.g. stress-strain curve at a fixed temperature. In an embodiment, lack of reproducibility may be indicated by reproducibility of less than 95% at 95% confidence interval. A substantially amorphous polymer may incorporate relatively small amounts of crystallinity. As is typical of amorphous polymers, the substantially amorphous polymer compositions of the invention show a transition from a glassy state to a rubbery state over a glass transition temperature range. Crystallinity can be reduced or eliminated by reducing the concentration of specific monomers that enhance this condition, and/or by introducing dissimilar structures to ensure that the polymer's molecular structure doesn't align during polymerization to result in crystallinity.

In many applications, biodurability can be defined as durability for the period of time necessary to assure that the body has overcome the need of the device's function, e.g. a fallopian tube occlusion device that relies upon scar tissue formation to close the lumen no longer needs the device to generate scar tissue once the lumen is fully closed. If that period of time is 90 days, for example, then the biodurable life of the device can be this value plus a suitable safety factor used in the design. Biodurability then is the ability of the device, and its material, to withstand the environmental challenges at its location of placement in the body, e.g. if in the bloodstream, it must withstand a bloody environment. In an embodiment, the radiopaque polymer is not biodegradable within the desired lifetime of the medical device. In another embodiment, the radiopaque polymer is not biodegradable within three years. In an embodiment, the non-biodegradable polymer does not include aromatic groups other than those present in naturally occurring amino acid. In an embodiment, the non-biodegradable polymer does not contain esters that are readily hydrolyzed at physiological pH and temperature.

For almost all locations within the body, one of the several primary mechanisms of degradation can be caused by absorption of water or moisture. Whether the environment contains interstitial fluids, blood, saliva, urine, bile, intracranial fluid, etc., these environments are aqueous based. If the device or its material absorbs water, the material properties and device dimensions can change due to swelling, or the device function can be affected, such as the autogenesis of an errant electrical path, or the material properties can degrade causing the device to weaken or break apart. Therefore a primary consideration for biodurability of an implanted device is the device and all of its material's ability to not absorb water.

In an embodiment, water uptake, or water absorption, can change the device's characteristics or detrimentally affect the device's performance over its intended life. In an embodiment, medical devices fabricated from the polymers of the invention will exhibit minimal water uptake. The water uptake can be measured over a test period equivalent to the lifetime or the device or can be measured over a shorter screening period. In an embodiment, the extent of water uptake is <1% by weight over 24 hours. For devices which exhibit water uptake of greater than 1% by weight over 24 hours, typically continuous exposure results in material changes such as brittleness and eventual mechanical failure in standard testing.

The minimal level of iodine concentration needed to achieve sufficient radiopacity to provide clinically acceptable imaging may be determined empirically. In an embodiment, evaluation of identically sized devices formulated from polymers using different weight percentages of iodinated monomer can be compared under simulated clinical use conditions. Using physicians' subjective review and correlating their opinion with the results from an image analysis program, Image J, to quantify signal levels, clinically imaging quality is correlated with iodine concentration. The result is a determination of the minimum iodine concentration to assure acceptable image quality. In an embodiment, the minimum iodine concentration value was established at 511 mg/cm$^3$. In an embodiment, the minimum iodine concentration value is above 200 mg/cm$^3$. In an embodiment, the iodine concentration value is between 50 and 600 mg/cm$^3$. As is recognized in the art, the radiopaque atom incorporation range for suitable visualization is dependent on the configuration of the device. In an embodiment, the first repeating unit contains the radiopaque atom(s) and is present in an amount of above 15 wt % of the network. In an embodiment, the first repeating unit contains the radiopaque atom(s) and is present in an amount of above 20 wt % of the network. In an embodiment, the first repeating unit contains the radiopaque atom(s) and is present in an amount of above 30 wt % of the network. In an embodiment, any incorporation of radiopaque moieties that produces a functional product can be used. As described elsewhere, the radiopaque atom(s) can include atoms other than iodine, including bromine.

In another embodiment, the signal obtained from a radiopaque polymer device may be compared with that of a platinum device of similar dimensions. In an embodiment where signal level is obtained by X-ray under a 6 inch water phantom, the signal from the radiopaque polymer device may be 70%-90% or 80%-90% of that of the platinum device.

From a biomedical device perspective, there are characteristics that are considered favorable in device design. They are quantified in terms of stimuli (such as temperature) driven response, well-defined response temperature, modulus, and elongation. In an embodiment, the thermomechanical properties of the shape memory polymer used to form the device are optimized for one or more of the following: Rubbery modulus ($E_{rub}$), Glass transition temperature ($T_g$), and Speed of recovery (S).

The preferred ranges of rubbery modulus can be different for different applications. The range of moduli of biological tissue can vary from 20 GPa (bone) to 1 kPa (eye) In an embodiment, the rubbery modulus is between 0.1 MPa and 15 MPa at 37° C. In an embodiment, the rubbery modulus is between 0.1 MPa and 50 MPa for the flexible state and between 0.1 to 500 MPa for the rigid state at 37° C. Any rubbery modulus value that produces a functional product can be used. By polymer formulation adjustments, the SMP's modulus, e.g. stiffness, can be established as very soft, on the order of 0.1 MPa. In one embodiment, for use as a device such as an embolic coil, this soft material enhances compaction of the coil pack, shortening the resulting pack for easier placement and ultimately increasing the speed of occlusion. Through other formulations, a higher value can be achieved for the SMP's modulus, such as 15 MPa, to enhance stiffness. In another embodiment, stiffer SMPs can be used to form a tube stent wherein localized stiffness is used to generate outward radial force against a vessel wall when deployed which is required for retention.

In an embodiment, the polymers are selected based on the desired glass transition temperature(s) (if at least one segment is amorphous) taking into consideration the environment of use. In one method, the polymer transition temperature is tailored to allow recovery at the body temperature, $T_r \sim T_g \sim 37°$ C. (A. Lendlein and R. Langer, "Biodegradable, elastic shape-memory polymers for potential biomedical applications." Science, vol. 296, pp. 1673-1676, 2002). The distinct advantage of this approach is the utilization of the body's thermal energy to naturally activate the material. The disadvantage of this approach, for some applications, is that the mechanical properties (e.g., stiffness) of the material are strongly dependent on $T_g$, and can be difficult to alter in the device design process. In particular, it would be difficult to design an extremely stiff device when the polymer $T_g$ is close to the body temperature due to the compliant nature of the polymer. Another possible disadvantage is that the required storage temperature, $T_s$, of a shape memory polymer with $T_g \sim 37°$ C. will typically be below room temperature requiring "cold" storage prior to deployment. In different embodiments, the glass transition temperature of the SMP of the present invention as determined from the peak of tan δ is 75° C., 50° C., 45° C. or any useful temperature. In general, as low a glass transition temperature is best, as understood in the art with the desired applications. In different embodiments, the glass transition temperature may be below body temperature (e.g. 25-35° C.), near body temperature (32-42° C.) or above body temperature (40-50° C.). Any $T_g$ value that produces a functional product can be used.

The storage modulus of at least partially non-crystalline polymers decreases in the glass transition region. DMA results highlight the changes that occur as the material is heated from its storage temperature ($T_s$) to its response temperature ($T_r$) and above. Methods are known in the art to determine relevant values to describe SMPs including thermal mechanical analysis (TMA) and differential scanning calorimetry (DSC); TMA and DSC are heating rate dependent. Such methods are described for example in WO 2012/019145, hereby incorporated by reference.

Typically, for each medical device application that incorporates shape recovery, the clinician is anticipating relatively rapid and repeatable shape recovery. In an embodiment, the shape memory polymer devices of the invention produce shape recovery that is fast enough to be detected, completes in a reasonable (intraoperative) time, and repeatable from one device to another. In an embodiment, the shape recovery time can be measured in use or from a screening procedure. The shape recovery time can be measured either from release to 100% recovery or from release to a predetermined amount of recovery.

The rate of shape change correlates with the rate of storage modulus change on the DMA curve between the operating temperature and $T_r$. For SMPs, rate of shape change can be primarily affected by the temperature difference between $T_0$, the operating temperature (external heating or body core temperature if self actuated), and the polymer's $T_g$ (derived from the formulation). $T_0$ is typically set above $T_r$. Typically, a larger difference between these temperatures will produce a faster rate of change up to an inherent rate limit, or asymptote of the change rate, of the material and device. This limit can be identified by monitoring shape change response time at different temperatures and plotting this relationship. Typically, the amount of response time decreases until it reaches an asymptote. The corresponding $T_0$ reflects the lowest, optimum temperature for the fastest rate of shape change for that material. Increasing the temperature above this point does not induce further reductions in the shape change recover time, e.g. does not further increase the rate of shape change. In an embodiment this inherent limit, or asymptote begins when $T_0$ is set at the temperature at which the Tan Delta curve is about 60% of its maximum value. In an embodiment, the polymer's maximum rate of shape change occurs at an environmental operating temperature (To) that is coincident with the temperature above Tg at which the material's Tan Delta value is equal to 60% of its peak value. The device may be designed so that this optimum temperature is at a useful operating temperature for the device (e.g. at body temperature or another preselected temperature).

In an embodiment, the device is operated at a temperature which is the lowest temperature at which no further increase in shape change rate is seen. In another embodiment, the device is operated at a temperature which is within +/−5° C. of this optimum temperature.

In different embodiments, the recovery ratio of the SMPs employed in the biomedical devices of the invention is greater than 75%, 80%, 90%, 95%, from 80-100%, from 90-100%, or from 95-100%. In various embodiments, the maximum achievable strain is of the radiopaque SMP from 10% to 800%, from 10% to 200%, from 10% to 500%, from 10% to 100%, from 20% to 800%, from 20% to 500%, from 20% to 800%. as measured at a temperature above the glass transition temperature. In different embodiments, the maximum achievable strain or strain to failure of the radiopaque SMP is at least 30% at least 40%, at least 50%, at least 60%, or at least 70%, from 40% to 100%, from 40% to 60%, from 50% to 100%, from 60% to 100% as measured below the glass transition temperature. In different embodiments, the maximum achievable strain or strain to failure of the SMP is at least 30% at least 40%, at least 50%, at least 60%, or at least 70%, from 40% to 100%, from 40% to 60%, from 50% to 100%, from 60% to 100% as measured at ambient temperature (20-25° C.).

In general, the ability of the device (whether technically shape memory or not) to change conformation or configuration (e.g. to expand) is made possible by manufacturing a device having a first conformation or configuration (initial configuration) and, thereafter configuring the device into a second conformation or configuration (temporary or storage configuration), wherein this configuration is at least partially reversible upon the occurrence of a triggering event. After the triggering event, the device assumes a third configuration. In an embodiment, the third configuration (deployed configuration) is substantially similar to the first configuration. However, for an implanted medical device, the device may be constrained from assuming its initial shape (first configuration). In an embodiment, the device is capable of self-expansion to the desired dimensions under physiological conditions.

In one aspect, the radiopaque polymers disclosed are shape memory polymers (SMPs). In one aspect, the compositions and compounds disclosed are useful for medical devices. In one aspect, the compositions and compounds disclosed may be shape memory polymers as defined herein and known in the art, but are not used in a manner in which the shape memory property is used. In one aspect, the compounds and compositions may or may not be externally triggered. In one aspect, the compositions and compounds disclosed are "space-triggered", as the phrase is conventionally used. In a space triggered material the materials return to their original shape upon removal of a spatial constraint, as is the case when a coil-shaped specimen emerges from its temporary elongated configuration within a deployment catheter and regains its coil shape, for example. In one aspect, the composition and compounds disclosed herein are "thermally-triggered," as the phrase is conventionally used. In a thermally triggered material the materials return to their original shape upon a thermal stimulus.

It should be made clear that certain compositions and compounds described herein may technically have shape memory properties, but those properties may or may not be used in the devices and methods of the invention. As used herein, the compounds and compositions described and disclosed here are intended to include shape memory aspects and non-shape memory aspects as applicable. If a particular embodiment is described using a shape memory polymer, it is recognized that other compounds and compositions that are not specifically defined as having shape memory properties may be interchangeable and used in that embodiment.

In general, the terms and phrases used herein have their art-recognized meaning, which can be found by reference to standard texts, journal references and contexts known to those skilled in the art. The following definitions are provided to clarify their specific use in the context of the invention.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states.

"Crosslinked polymer network" refers a polymer composition comprising a plurality of polymer chains wherein a large portion (e.g., ≥80%) and optionally all the polymer chains are interconnected, for example via covalent crosslinking, to form a single polymer composition. In an embodiment, the invention provides a radiopaque polymer in the form of a crosslinked network in which at least some of the crosslinks of the network structure are formed by covalent bonds.

"Monomer" refers to a reagent which can undergo polymerization under appropriate conditions. A monomer reagent comprises at least one monomer molecule, where a monomer molecule is a molecule which can undergo polymerization, thereby contributing constitutional units to the structure of a macromolecule or oligomer. In an embodiment, a monomer reagent may be represented by an average or dominant chemical structure and comprise monomer molecules having that chemical structure but may also contain components with other chemical structures. For example, a monomer reagent may comprise impurities having chemical structures other than the average or dominant structure of the reagent. An oligomer or oligomeric reagent is also a reagent which can undergo polymerization under appropriate conditions. An oligomeric reagent comprises an oligomer molecule, the oligomer molecule comprising a small plurality of units derived from molecules of lower relative molecular mass. In an embodiment, certain hyperbranched crosslinking reagents suitable for use with the invention may be regarded as oligomeric reagents.

In an embodiment, the iodinated crosslinked polymers of the invention are formed by the polymerization of a polymer precursor mixture comprising an iodinated monofunctional monomer, a multifunctional crosslinker monomer or oligomer having more than two polymerizable groups, and an initiator. The polymer precursor mixture may also comprise one or more additional iodinated monofunctional monomers, one or more additional crosslinker monomers or oligomers, and/or one or more additional monofunctional monomers. As used herein, "monofunctional" refers to a monomer containing only one polymerizable group, while "multifunctional" refers to a monomer containing more than one polymerizable group.

"Radiopacity" refers to the relative inability of electromagnetism, particularly X-rays, to pass through dense materials. The two main factors contributing to a material's radiopacity are density and atomic number of the radiopaque element. In an embodiment, this invention utilizes incorporated (trapped) iodine molecules within the polymer matrix to induce radiopaque functionality. In an embodiment, the radiopaque polymer is an iodinated polymer. As referred to herein, iodinated polymers are produced by incorporating (trapping) iodine molecules on a select monomer prior to formulation of the monomer into a polymer. Although iodine is used in some examples and descriptions herein, it is recognized that other radiopaque materials may be used, such as Bi and Br and that the descriptions here apply to and may be used with other radiopaque materials. Radiopacity may refer to specific signal strength when utilizing imaging techniques, for example, having a signal greater than or equal to different substance of the same size and shape, for example, iron or steel. Radiopaque may refer to providing a signal greater than or equal to a 0.020" diameter steel wire.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups or radicals characterized as monovalent, divalent, trivalent, etc. valence states. When a structure of a group is illustrated herein, a wavy line may be drawn across a bond that connects to other atoms in the molecule.

As used herein, the term "substituted" refers to a compound wherein a hydrogen is replaced by another functional group.

Unless otherwise specified, the term "average molecular weight," refers to number average molecular weight. Number average molecular weight is the defined as the total weight of a sample volume divided by the number of molecules within the sample. As is customary and well known in the art, peak average molecular weight and weight average molecular weight may also be used to characterize the molecular weight of the distribution of polymers within a sample.

"wt %" is an abbreviation for weigh percentage. Weight percentage is the defined as 100 times the mass fraction of one (or more) components of a mixture to the mass of the total mixture. For example, weigh percentage of component X may be expressed by the following:

$$\text{wt \% (of component } x) = 100 \times \frac{M_x}{M_{total}};$$

wherein $M_x$ is the mass of component x and $M_{total}$ is the mass of the total mixture.

As is customary and well known in the art, hydrogen atoms in formulas (FX1a)-(FX5c) are not always explicitly shown, for example, hydrogen atoms bonded to the carbon atoms of aromatic, heteroaromatic, and alicyclic rings are not always explicitly shown in formulas (FX1a)-(FX5c). The structures provided herein, for example in the context of the description of formulas (FX1a)-(FX5c) and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the term "heteroalkane" refers to a compound derived from an alkane and comprising at least one "heteroatom", i.e., a non-carbon/non-hydrogen atom.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups.

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as linking and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups, for example, as one or more linking groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon and hydrogen, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides are comprised of two or more amino-acid connected via peptide bonds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—$CON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$OCON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$N(R)_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2R$, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—$SO_2N(R)_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible Example 1

A 5 mL vial was charged with 10-acryloyloxydecyl-(2,3,5)-triiodobenzoate (C10-TIA; 2.175 g), sebacic acid-bis-dipentaerythritol-pentaacrylate ester (10XLS; 0.225 g) and methacryloxypropyl-terminated polydimethylsiloxane (Gelest DMS-R05; 0.100 g). The vial contents were melted in a 125° C. oven for 10 minutes and mixed thoroughly. Luperox P thermal initiator was added (15 μL) and mixed thoroughly. The molten composition was injected into a silicone rubber DMA specimen mold between two glass microscope slides and then cured at 125° C. for 2.5 hours. Dynamic mechanical analysis (DMA) results are summarized in Table 1 and FIG. 1.

Example 2

A 5 mL vial was charged with C10-TIA (2.125 g), dipentaerythritol-hexaacrylate (DP6A; 0.250 g) and Gelest DMS-R05 (0.125 g). The vial contents were melted in a 125° C. oven for 10 minutes and mixed thoroughly. Luperox P thermal initiator was added (15 μL) and mixed thoroughly. The molten composition was injected into a silicone rubber DMA specimen mold between two glass microscope slides and then cured at 125° C. for 2.5 hours. DMA results are summarized in Table 1 and FIG. 1.

Example 3

A 5 mL vial was charged with C10-TIA (2.125 g), DP6A (0.275 g) and Gelest DMS-R05 (0.100 g) The vial contents were melted in a 125° C. oven for 10 minutes and mixed thoroughly. Luperox P thermal initiator was added (15 μL) and mixed thoroughly. The molten composition was injected into a silicone rubber DMA specimen mold between two glass microscope slides and then cured at 125° C. for 2.5 hours. DMA results are summarized in Table 1 and FIG. 1.

TABLE 1

| Composition | % wt C10-TIA | % wt DP6A | % wt 10XLS | % wt SiDMA-465 | % wt Luperox P | Tg (° C.) | Isothermal 37° C. Modulus (MPa) |
|---|---|---|---|---|---|---|---|
| Example 1 | 87 | 0 | 9 | 4 | 0.6 | 30 | 30 |
| Example 2 | 85 | 10 | 0 | 5 | 0.6 | 33 | 56 |
| Example 3 | 85 | 11 | 0 | 4 | 0.5 | 33 | 84 |

Example 4

Animal Studies of Radiopacity

Radiopaque polymers of the invention were evaluated in animal subject for in vivo radiopacity. The polymers tested included C10-TIA (73 wt %), C10-DA (27 wt %), and Luperox P (0.5 wt %). In animal testing, with what was later to be found to be C10-TIA with 94% purity, the limiting wire diameter with acceptable visibility was found to be 0.018"; in subsequent animal testing involving the use of C10-TIA with 99+% purity, the limiting wire diameter with acceptable visibility including the desired range 0.015-0.016". The use of a siloxane-based crosslinker (provided at 3 wt %) with C10-TIA below 95% purity, though never tested in an animal, was found to increase the overall extent of radiopacity, qualitatively, over a sample of C10-TIA without siloxane, and seemed to mimic the radiopacity performance of C10-TIA made with C10-TIA with 99+% purity without siloxane.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A crosslinked polymer network comprising:

a) a plurality of first repeating units comprising a first reagent, the first reagent defined by the formula FX1a, FX1b, FX1c or FX1d:

[FX1a]

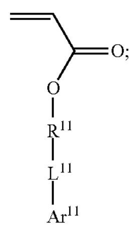

[FX1b]

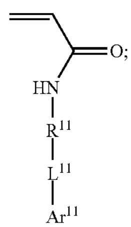

[FX1c]

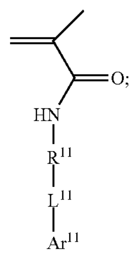

[FX1d]

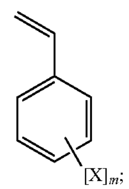

wherein:

X is Br or I;

m is an integer selected from the range of 1 to 5;

each $R^{11}$ is, independently, a substituted or unsubstituted $C_6$-$C_{20}$ alkylene group;

each $L^{11}$ is, independently, a single bond, $-(CH_2)_j-$, $-(HCCH)_j-$, —O—, —S—, —SO—, $-SO_2-$, $-SO_3-$, $-OSO_2-$, $-NR^{12}$, —CO—, —COO—, —OCO—, —OCOO—, $-CONR^{13}-$, $-NR^{14}CO-$, $-OCONR^{15}-$, $-NR^{16}COO-$, $-NR^{17}CONR^{18}-$, $-SiO(Z^1)(Z^2)-$, or $-Si[SiO(Z^1)(Z^2)]_n-$, wherein $Z^1$ is given by the formula $L^1(T^1)_p$ and $Z^2$ is given by the formula $L^2(T^2)_q$, and wherein each of $L^1$ and $L^2$ are, independently, a single bond, a polyvalent alkane radical having from 1 to 36 carbon atoms, a polyvalent heteroalkane radical having from 1 to 36 carbon atoms and including —O— or —C(O)O—, a polyvalent aryl radical having from 1 to 36 carbon atoms, or a polyvalent heteroaryl radical having from 1 to 36 carbon atoms and including —O— or —C(O)O—, and wherein each of $T^1$ and $T^2$ are, independently, a polymerizable group having a terminal (meth) acrylate, (meth)acrylamide or styryl group, and wherein n is an integer selected from the range of 1-10;

each $Ar^{11}$ is, independently, an iodine- or bromine-containing $C_5$-$C_{36}$ aryl group containing one or more rings, or an iodine- or bromine-containing $C_5$-$C_{36}$ heteroaryl group containing one or more rings; and wherein each of $R^{12}$-$R^{18}$ is, independently, hydrogen or a $C_1$-$C_{10}$ alkyl group and each j is, independently, an integer selected from the range of 1 to 10;

b) a plurality of second repeating units comprising a second reagent, the second reagent defined by the formula $Z^3{}_aX^1{}_cSi_dO_eZ^4{}_b$;

wherein:

$Z^3$ is given by the formula $L^3(T^3)_p$ and $Z^4$ is given by the formula $L^4(T^4)_q$, wherein each of $L^3$ and $L^4$ are, independently, a single bond, a polyvalent alkane radical having from 1 to 36 carbon atoms, a polyvalent heteroalkane radical having from 1 to 36 carbon atoms and including —O— or —C(O)O—, a polyvalent aryl radical having from 1 to 36 carbon atoms, or a polyvalent heteroaryl radical having from 1 to 36 carbon atoms and including —O— or —C(O)O—, wherein each of $T^3$ and $T^4$ are, independently, a polymerizable group having a terminal (meth) acrylate, (meth)acrylamide, or styryl group;

each $X^1$ is, independently, an alkyl group, a (meth) acrylate group, a (meth)acrylamide group, or a styryl group having 1 to 36 carbon atoms;

each a, b and d are, independently, integers selected from the range of 1 to 10 and each c and e are, independently, integers selected from the range of 1 to 20; and p and q are each, independently, an integer selected from the range of 1 to 9; and c) a plurality of third repeating units comprising a third reagent, the third reagent comprising at least three terminal (meth)acrylate, (meth)acrylamide, or styryl groups.

2. The crosslinked polymer network of claim 1, wherein $Ar^{11}$ is an iodine containing $C_6$ aryl group with 3 to 5 iodine atoms attached directly to the ring.

3. The crosslinked polymer network of claim 1, wherein $R^{11}$ is a $C_6$-$C_{24}$ alkylene group.

4. The crosslinked polymer network of claim 1, wherein said first reagent is defined by the formula FX2:

[FX2]

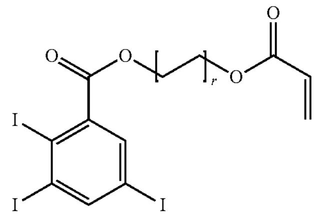

wherein r is an integer selected from the range of 2 to 18.

5. The crosslinked polymer network of claim 1, wherein said third reagent is defined by the formula FX3:

[FX3]

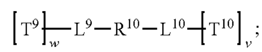

wherein:

$R^{10}$ is C, N, O, a substituted or unsubstituted $C_2$-$C_{36}$ multivalent alkane radical, or a substituted or unsubstituted $C_2$-$C_{36}$ alkylene;

each of $L^9$ and $L^{10}$ are, independently, a single bond, a polyvalent straight or branched $C_2$-$C_{12}$ alkane radical, a polyvalent straight or branched $C_2$-$C_{12}$ heteroalkane radical including —O— or —C(O)O—, —$(CH_2)_n$—, —$(HCCH)_n$—, —O—, —S—, —SO—, —$SO_2$—, —$SO_3$—, —$OSO_2$—, —$NR^3$—, —CO—, —COO—, —OCO—, —OCOO—, —$CONR^4$—, —$NR^5CO$—, —$OCONR^6$—, —$NR^7COO$—, or —$NR^8CONR^9$, wherein each of $R^3$-$R^9$ is, independently, hydrogen or $C_1$-$C_{10}$ alkyl, and each n is, independently, an integer selected from 1 to 10;

each $T^9$ and each $T^{10}$ are, independently, a polymerizable group having a terminal (meth)acrylate, (meth) acrylamide or styryl group; and w and v are each, independently, integers from 1 to 9.

6. The crosslinked polymer network of claim 5, wherein:

$R^{10}$ is O;

each $T^9$ and each $T^{10}$ are (meth)acrylate; and w and v are each, independently, integers from 1 to 6.

7. The crosslinked polymer network of claim 1, wherein said second reagent is defined by the formula FX5a:

[FX5a]

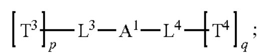

wherein $A^1$ is Si or is defined by the formula FX5b, FX5c, FX5d, FX5e or FX5f:

[FX5b]

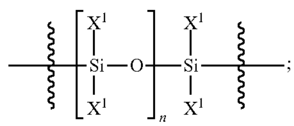

[FX5c]

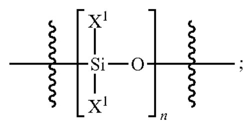

-continued

[FX5d]

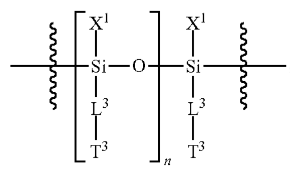

[FX5e]

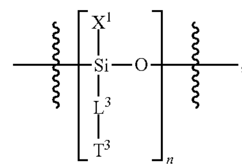

[FX5f]

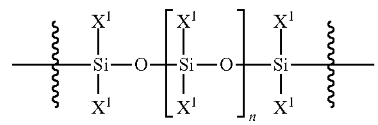

wherein:

each $X^1$ is, independently, an alkyl group, a (meth)acrylate group, a (meth)acrylamide group, or a styryl group having 1 to 36 carbon atoms;

each n is, independently, selected from the range of 1 to 10;

each of p and q are, independently, integers from 1 to 9;

each $L^3$ and $L^4$ is, independently, a single bond, C, N, O, a polyvalent alkane radical having from 1 to 36 carbon atoms, a polyvalent heteroalkane radical having from 1 to 36 carbon atoms and including —O— or —C(O) O—, a polyvalent aryl radical having from 1 to 36 carbon atoms, or a polyvalent heteroaryl radical having from 1 to 36 carbon atoms and including —O— or —C(O)O—, a straight or branched $C_2$-$C_{12}$ alkylene group, a straight or branched $C_2$-$C_{12}$ oxyalkylene group, a straight or branched $C_2$-$C_{12}$ carboxyalkylene group, a straight or branched $C_2$-$C_{12}$ oxyarylene group, or a straight or branched $C_2$-$C_{12}$ carboxyarylene group; and each $T^3$ and $T^4$ is, independently, a polymerizable group having a terminal(meth)acrylate, (meth)acrylamide, or styryl group.

8. The crosslinked polymer network of claim 7, wherein said second reagent is defined by the formula FX5g:

[FX5g]

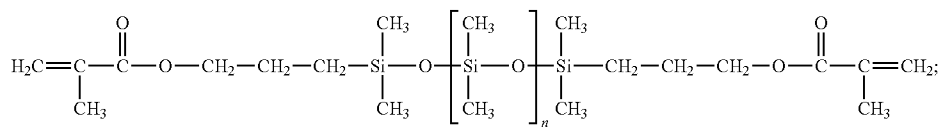

wherein n selected from the range of 1 to 10.

9. The crosslinked polymer network of claim 1, wherein said crosslinked polymer network has greater than or equal to 15 wt % of said first reagent, said crosslinked polymer network has less than or equal to 85 wt % of said second reagent, said crosslinked polymer network has less than or equal to 85 wt % of said third reagent, or a combination thereof.

10. The crosslinked polymer network of claim 1, wherein said crosslinked polymer network comprises between 80 to 90 wt % of said first reagent, 1 to 10 wt % of said second reagent, and 5 to 15 wt % of said third reagent.

11. A radiopaque polymer device for medical application, comprising a polymer composition according to claim 1, optionally comprising a fiber, a coil or a mesh.

12. The radiopaque polymer device of claim 11, wherein the device provides the function of:

opening an anatomical lumen; or closing an anatomical lumen, either partially as a valve, or complete lumen occlusion; or support of an anatomical structure to assist in the therapeutic restoration of an organ, vascular, digestive, excrement, or airway function; or support of an anatomical structure to assist in therapeutic restoration of an orthopedic, maxiofacial, spinal, or joint function; or to support homeostasis by covering an area after tissue dissection or resection.

13. The radiopaque polymer device of claim 11, for purposes of a diagnostic or therapeutic instrument or device to provide the function of:

a catheter for the purposes of accessing an anatomical location; delivering another device and/or therapeutic agent; or controlling the access or delivery of another device and/or therapeutic agent.

14. The radiopaque polymer device of claim 11, having a cylindrical shape with a diameter less than or equal to 0.015 inches.

15. A crosslinked polymer network comprising:

a) a plurality of first repeating units comprising a first reagent, the first reagent defined by the formula FX1a, FX1b, FX1c or FX1d:

[FX1a]

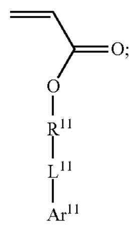

[FX1b]

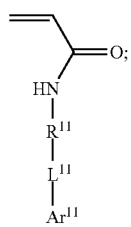

-continued

[FX1c]

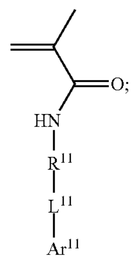

[FX1d]

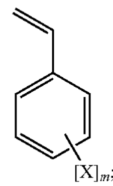

wherein:

X is Br or I;

m is an integer selected from the range of 1 to 5;

each $R^{11}$ is, independently, a substituted or unsubstituted $C_7$-$C_{20}$ alkylene group; each $L^{11}$ is independently a single bond, $-(CH_2)_j-$, $-(HCCH)_j-$, $-O-$, $-S-$, $-SO-$, $-SO_2-$, $-SO_3-$, $-OSO_2-$, $-NR^{12}$, $-CO-$, $-COO-$, $-OCO-$, $-OCOO-$, $-CONR^{13}-$, $-NR^{14}CO-$, $-OCONR^{15}-$, $-NR^{16}COO-$, $-NR^{17}CONR^{18}-$, $-SiO(Z^1)(Z^2)-$, or $-Si[SiO(Z^1)(Z^2)]_n-$, wherein $Z^1$ is given by the formula $L'(T^1)_p$ and $Z^2$ is given by the formula $L^2(T^2)_q$, wherein each of $L^1$ and $L^2$ are, independently, a single bond, a polyvalent alkane radical having from 1 to 36 carbon atoms, a polyvalent heteroalkane radical having from 1 to 36 carbon atoms and including $-O-$ or $-C(O)O-$, a polyvalent aryl radical having from 1 to 36 carbon atoms, or a polyvalent heteroaryl radical having from 1 to 36 carbon atoms and including $-O-$ or $-C(O)O-$, wherein each of $T^1$ and $T^2$ are, independently, a polymerizable group having a terminal (meth)acrylate, (meth)acrylamide, or styryl group, and n is an integer selected from the range of 1-10;

each $Ar^{11}$ is, independently, an iodine- or bromine-containing $C_5$-$C_{36}$ aryl group containing one or more rings, or an iodine- or bromine-containing $C_5$-$C_{36}$ heteroaryl group containing one or more rings, wherein each of $R^{12}$-$R^{18}$ is, independently, hydrogen or a $C_1$-$C_{10}$ alkyl group and each j is, independently, an integer selected from the range of 1 to 10;

b) a plurality of second repeating units comprising a second reagent, the second reagent defined by the formula $Z^3_aX^1_cSi_dO_eZ^4_b$;

wherein:

$Z^3$ is given by the formula $L^3(T^3)_p$ and $Z^4$ is given by the formula $L^4(T^4)_q$;

wherein each of $L^3$ and $L^4$ are, independently, a single bond, a polyvalent alkane radical having from 1 to 36 carbon atoms, a polyvalent heteroalkane radical having from 1 to 36 carbon atoms and including $-O-$ or $-C(O)O-$, a polyvalent aryl radical having from 1 to 36 carbon atoms, or a polyvalent heteroaryl radical having from 1 to 36 carbon atoms and including —O— or —C(O)O—, wherein each of $T^3$ and $T^4$ are, independently, a polymerizable group having a terminal (meth)acrylate, (meth)acrylamide, or styryl group;

each $X^1$ is, independently, an alkyl group, a (meth)acrylamide group, or a styryl group having 1 to 36 carbon atoms;

each a, b and d are, independently, integers selected from the range of 1 to 10 and each c and e are, independently, integers selected from the range of 1 to 20; and p and q are each, independently, an integer selected from the range of 1 to 9; and c) a plurality of third repeating units, each of the third repeating units comprising at least three terminal (meth)acrylate, (meth)acrylamide, or styryl groups.

* * * * *